US006512018B2

(12) United States Patent
Kennedy

(10) Patent No.: US 6,512,018 B2
(45) Date of Patent: Jan. 28, 2003

(54) HYDROCARBON CONVERSION PROCESS USING A PLURALITY OF SYNTHESIS GAS SOURCES

(75) Inventor: Paul Edwin Kennedy, Tulsa, OK (US)

(73) Assignee: Syntroleum Corporation, Tulsa, OK (US)

(*) Notice: Subject to any disclaimer, the term of this patent is extended or adjusted under 35 U.S.C. 154(b) by 0 days.

(21) Appl. No.: 09/817,544

(22) Filed: Mar. 26, 2001

(65) Prior Publication Data

US 2001/0027220 A1 Oct. 4, 2001

Related U.S. Application Data

(60) Provisional application No. 60/192,503, filed on Mar. 28, 2000.

(51) Int. Cl.[7] .............................................. C07C 27/00
(52) U.S. Cl. ........................ 518/715; 518/700; 518/702; 518/703; 518/704
(58) Field of Search ................................. 518/700, 702, 518/703, 704, 715

(56) References Cited

U.S. PATENT DOCUMENTS

| 4,833,170 A | | 5/1989 | Agee | |
|---|---|---|---|---|
| 5,763,716 A | * | 6/1998 | Benham et al. | 585/315 |
| 6,248,794 B1 | * | 6/2001 | Gieskes | 518/700 |

* cited by examiner

Primary Examiner—J. Parsa
(74) Attorney, Agent, or Firm—Dority & Manning

(57) ABSTRACT

A Fischer-Tropsch-based process and system for converting light hydrocarbons into heavier hydrocarbons uses a plurality of different synthesis gas generators. The process includes preparing a first synthesis gas having a $H_2$:CO ratio greater than 2:1; removing a portion of the hydrogen from the first synthesis gas; preparing a second synthesis gas with a $CO_2$ recycle wherein the second synthesis gas has a $H_2$:CO ratio less than 2:1; adding the removed hydrogen to the second synthesis gas to increase the $H_2$:CO ratio of the second synthesis gas; and using a Fischer-Tropsch reaction to convert the first synthesis gas and the second synthesis gas to heavier hydrocarbons.

11 Claims, 4 Drawing Sheets

FIG. 2A

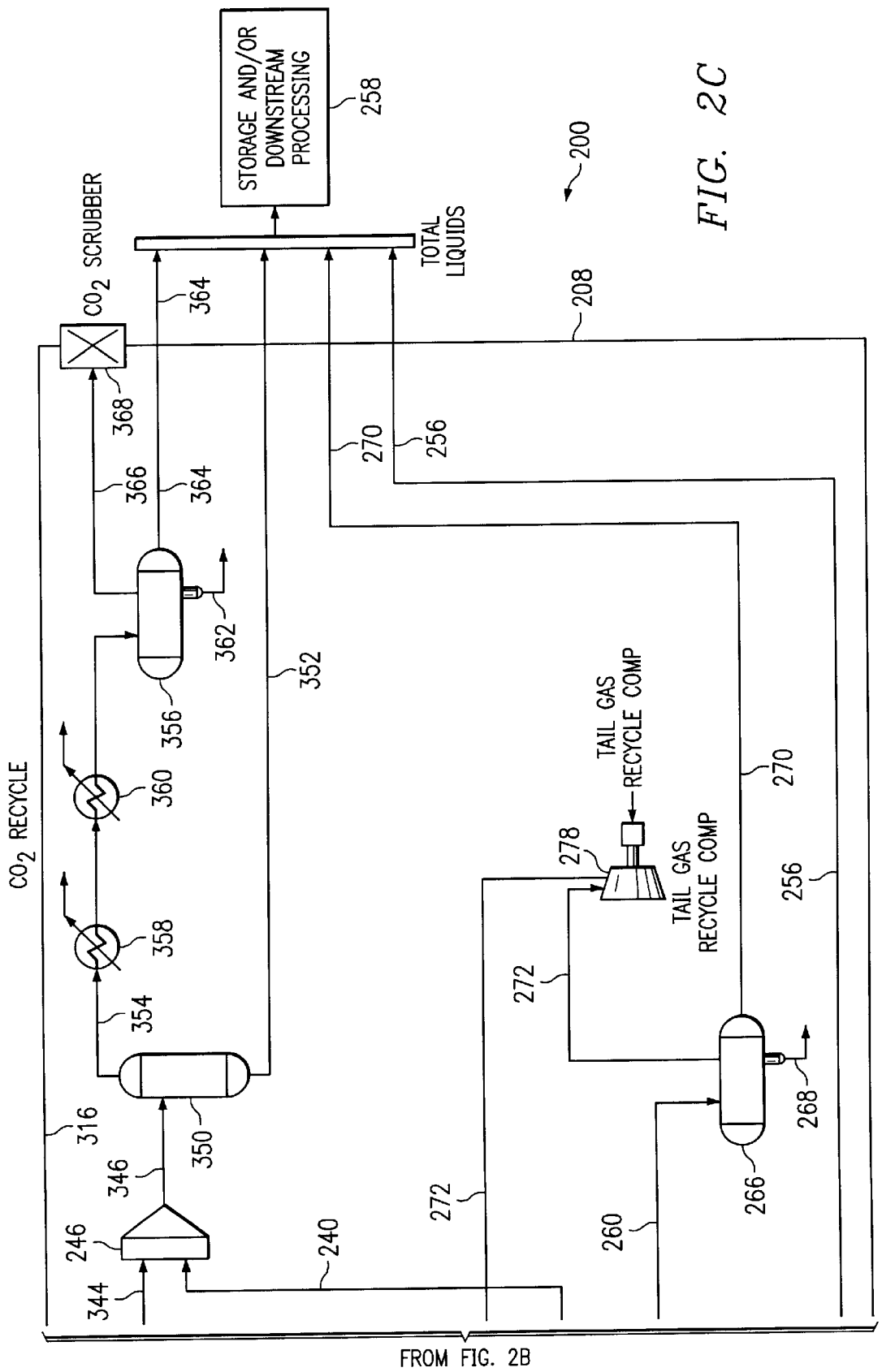

HYDROCARBON CONVERSION PROCESS USING A PLURALITY OF SYNTHESIS GAS SOURCES

RELATED PATENT APPLICATION

This application claims priority of U.S. Provisional Application No. 60/192,503, filed Mar. 28, 2000, entitled, "System and Method for Converting Light Hydrocarbons Into heavier Hydrocarbons with a Plurality of Synthesis Gas Sources."

TECHNICAL FIELD OF THE INVENTION

The present invention relates to the conversion of hydrocarbons such as through a Fischer-Tropsch reaction, and more particularly relates to hydrocarbon conversion process and system using a plurality of synthesis gas sources.

BACKGROUND OF THE INVENTION

A. INTRODUCTION TO THE FISCHER TROPSCH PROCESS

The synthetic production of hydrocarbons by the catalytic reaction of carbon monoxide and hydrogen is well known and is generally referred to as the Fischer-Tropsch reaction. The Fischer-Tropsch process was developed in early part of the 20$^{th}$ century in Germany. It has been practiced commercially in Germany during World War II and later in South Africa.

The Fischer-Tropsch reaction for converting synthesis gas (primarily CO and $H_2$) has been characterized by the following general reaction:

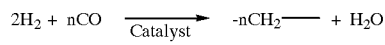

The hydrocarbon products derived from the Fischer-Tropsch reaction range from some methane to high molecular weight paraffinic waxes containing more than 100 carbon atoms.

Numerous catalysts have been used in carrying out the Fischer-Tropsch reaction. Usually a Group VIII metal, such as cobalt, iron, or ruthenium, is used. Both saturated and unsaturated hydrocarbons can be produced. The synthesis reaction is very exothermic and temperature sensitive whereby temperature control is required to maintain a desired hydrocarbon product selectivity.

While the Fischer-Tropsch process has been around for nearly eighty years, improved performance remains a goal. In particular, an ongoing quest exists to improve the economics of the process.

B. INTRODUCTION TO SYNTHESIS GAS PRODUCTION

Synthesis gas ("syngas"), which is substantially carbon monoxide and molecular hydrogen, may be made from natural gas, gasified coal, and other sources. Three basic methods have been employed for producing synthesis gas utilized as feedstock in the Fischer-Tropsch reaction. Traditional methods include steam reforming, wherein one or more light hydrocarbons such as methane are reacted with steam over a catalyst to form carbon monoxide and hydrogen, and partial oxidation, wherein one or more light hydrocarbons are combusted sub-stoichiometrically to produce synthesis gas. The steam reforming reaction is endothermic and a catalyst containing nickel is often utilized. Partial oxidation is the catalytic or non-catalytic, sub-stoichiometric combustion of light hydrocarbons such as methane to produce the synthesis gas. The partial oxidation reaction is typically carried out using high-purity oxygen. High-purity oxygen, however, can be quite expensive and dangerous to handle.

In some situations these synthesis gas production methods may be combined to form a third method. A combination of partial oxidation and steam reforming, known as autothermal reforming, and which uses air (or $O_2$) as a source of oxygen for the partial oxidation reaction, has also been used for producing synthesis gas heretofore. With autothermal reforming, the exothermic heat of the partial oxidation supplies the necessary heat for the endothermic steam reforming reaction. The autothermal reforming process can be carried out in a relatively inexpensive refractory lined carbon steel vessel.

The autothermal process results in a lower hydrogen-to-carbon-monoxide ratio in the synthesis gas than does steam reforming alone. That is, the steam reforming reaction with methane results in a ratio of about 3:1 or higher while the partial oxidation of methane results in a ratio of approximately 2:1. A good ratio for the Fischer-Tropsch (F-T) hydrocarbon synthesis reaction carried out at low or medium pressure (i.e. in the range of about atmospheric to 500 psig) over a cobalt catalyst is about 2:1. When the feed to the autothermal reforming process is a mixture of light shorter-chain hydrocarbons such as a natural gas stream, some form of additional control is desirable to maintain the ratio of hydrogen to carbon monoxide in the synthesis gas at the desired ratio, which for cobalt based F-T catalysts is about 2:1. Steam and/or $CO_2$ may be added to the synthesis gas reactor to adjust the ratio.

C. INTRODUCTION TO CONVERSION SYSTEMS

Fischer-Tropsch hydrocarbon conversion systems typically have a synthesis gas generator or source as discussed above. The synthesis gas generator receives light, short-chain hydrocarbons such as methane and produces synthesis gas. The synthesis gas is then delivered to a Fischer-Tropsch reactor. In the Fischer-Tropsch reactor, the synthesis gas is converted to heavier, longer-chain hydrocarbons. Hundreds of example systems are shown in the literature; for example, U.S. Pat. Nos. 4,833,170 and 4,973,453, which are incorporated by reference herein for all purposes, present useful conversion systems.

D. IMPROVED ECONOMICS DESIRED

It has been a quest for many to improve the economics of processes utilizing the Fischer-Tropsch reaction. Improved economics will allow for wide-scale adoption of the process in numerous sites and for numerous applications. Efforts have been made to improve economics, but further improvements are desirable.

SUMMARY OF THE INVENTION

A need has arisen for a system and method that addresses shortcomings of prior systems and methods. According to an aspect of the present invention, a process for converting light hydrocarbons to heavier hydrocarbons includes steps of: preparing a first synthesis gas having a $H_2$:CO ratio greater than 2:1; removing a portion of the hydrogen from the first synthesis gas; preparing a second synthesis gas with a $CO_2$ recycle wherein the second synthesis gas has a $H_2$:CO ratio less than 2:1; adding the removed hydrogen to the second synthesis gas to increase the $H_2$:CO ratio of the second synthesis gas; and using a Fischer-Tropsch reaction to convert the first synthesis gas and the second synthesis gas to heavier hydrocarbons. According to another aspect of the present invention, a first tail gas is also prepared in the first synthesis unit and is used in the second synthesis gas unit as a fuel. According to another aspect of the present invention, the second synthesis unit also prepares a second tail gas from which $CO_2$ is removed and recycled to the second synthesis gas unit.

According to another aspect of the present invention, a system for converting light hydrocarbons into heavier hydrocarbons includes a first synthesis gas unit, which preferably has a steam methane reformer, for producing a first synthesis gas; a hydrogen separator coupled to the first synthesis gas unit for removing at least a portion of the hydrogen from a first synthesis gas to make a hydrogen-reduced synthesis gas; a second synthesis gas unit, which preferably has an autothermal reformer, for receiving an oxygen-containing gas, light hydrocarbons, and carbon dioxide and producing a second synthesis gas; a first synthesis unit fluidly coupled to the hydrogen separator for receiving the hydrogen-reduced synthesis gas and producing heavier hydrocarbons; a second synthesis unit fluidly coupled to the second synthesis gas unit and hydrogen separator for receiving a second synthesis gas from the second synthesis gas unit and hydrogen from the hydrogen separator unit and producing heavier hydrocarbons; and a carbon dioxide removal unit coupled to the second synthesis unit for receiving the tail gas therefrom and removing carbon dioxide therefrom and delivering the carbon dioxide to the second synthesis gas unit. According to another aspect of the present invention, the first synthesis unit is also operable to produce a first tail gas that may be used in the second synthesis gas unit. According to another aspect of the present invention, the second synthesis unit is operable to produce a second tail gas that may be used as a burner fuel in the first synthesis gas unit.

The present invention provides many advantages. A number of examples follow. An advantage of the present invention is that the system and method require less light hydrocarbons to produce a given quantity of product, i.e., it has a higher carbon efficiency. Another advantage of the present invention is that an autothermal reformer may be utilized at high pressure thereby allowing the removal of a synthesis gas booster compressor but without suffering a loss in carbon efficiency for the higher pressure. With respect to this advantage, the carbon efficiency of the autothermal reformer is reduced at higher pressure, but since $CO_2$, which is produced at the higher pressure, is recycled, the effective efficiency is not reduced by increasing pressure.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

Figure 1:
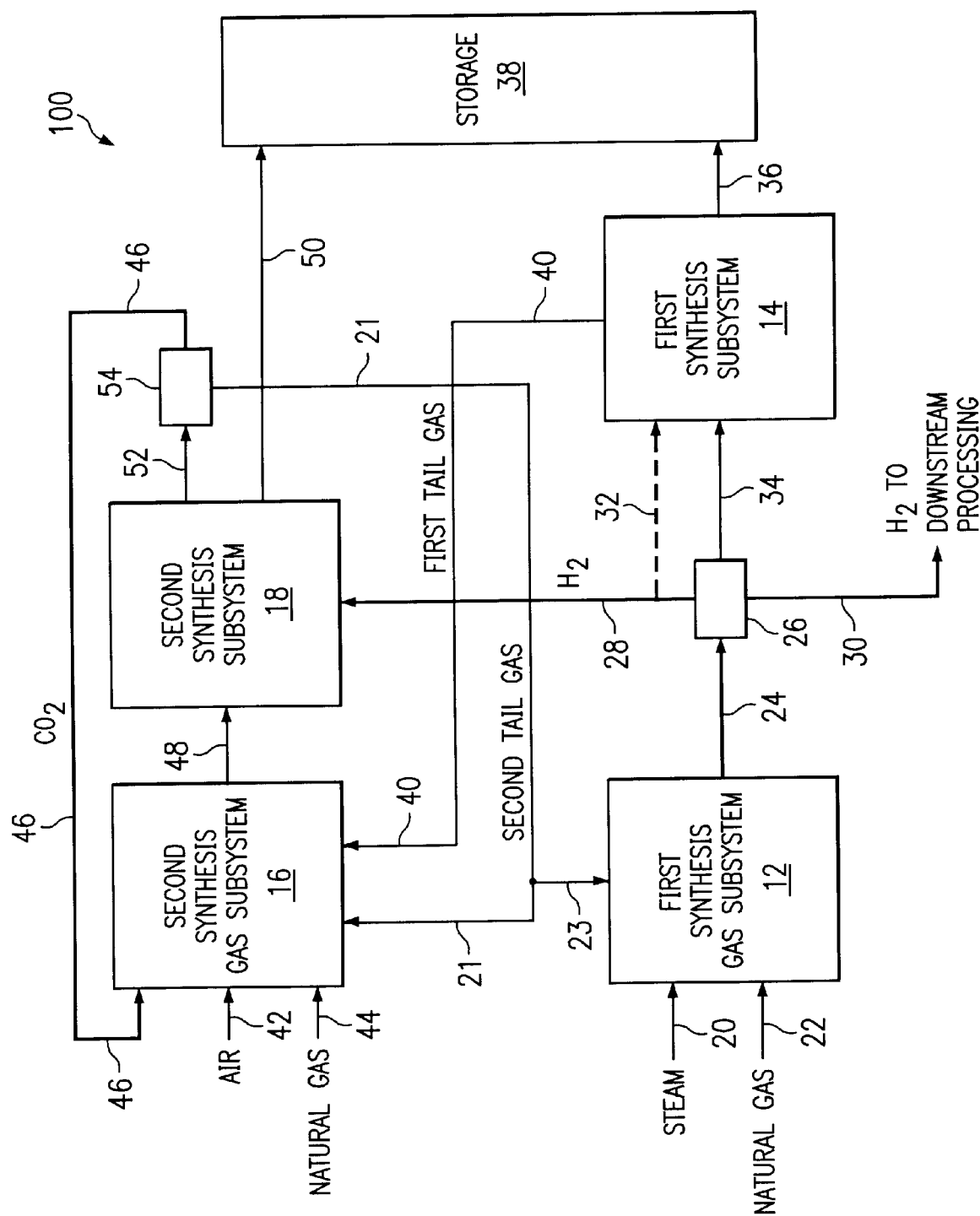
FIG. 1 is a schematic diagram of one embodiment a system according to the present invention.
Figure 2A:
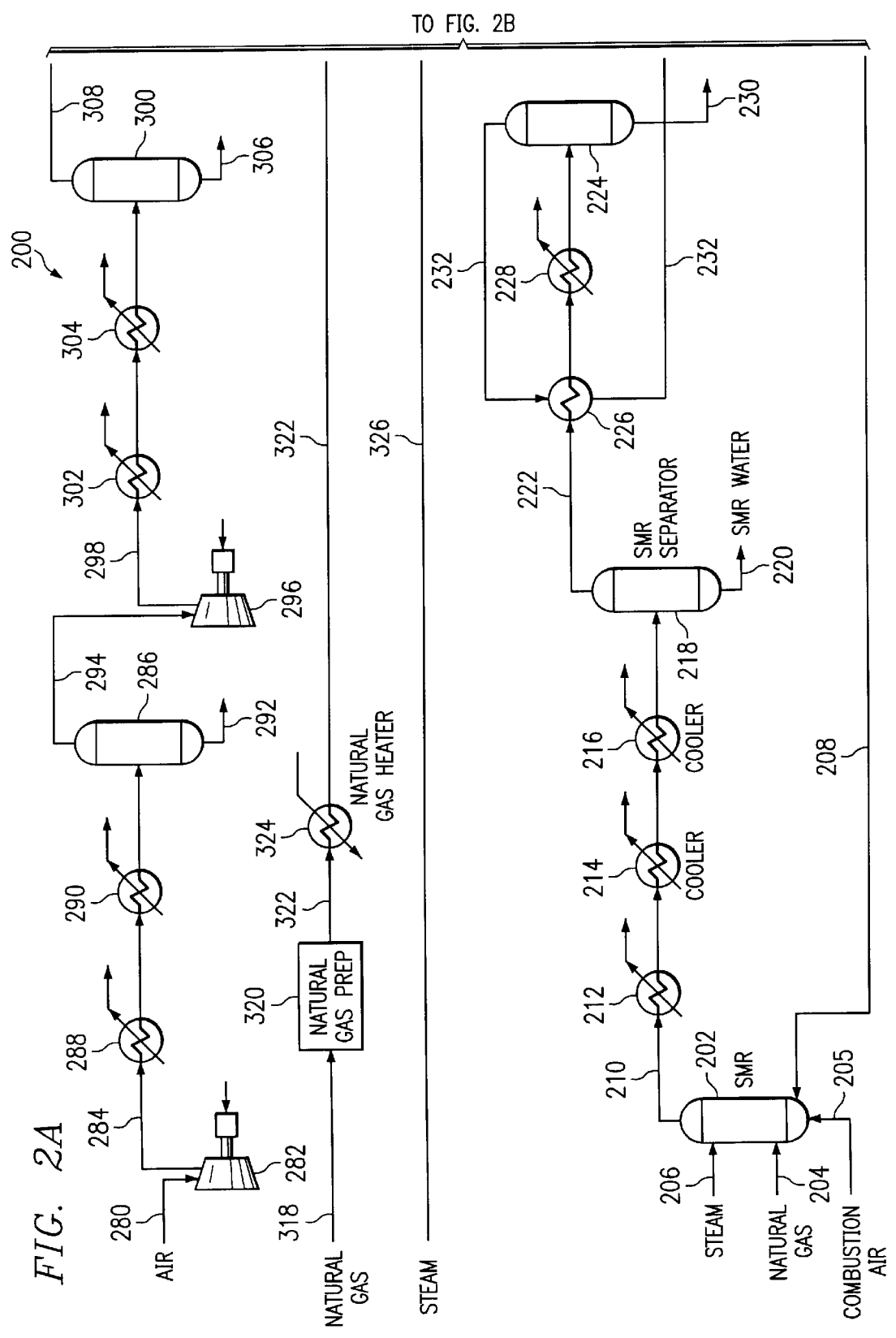
Figure 2B:
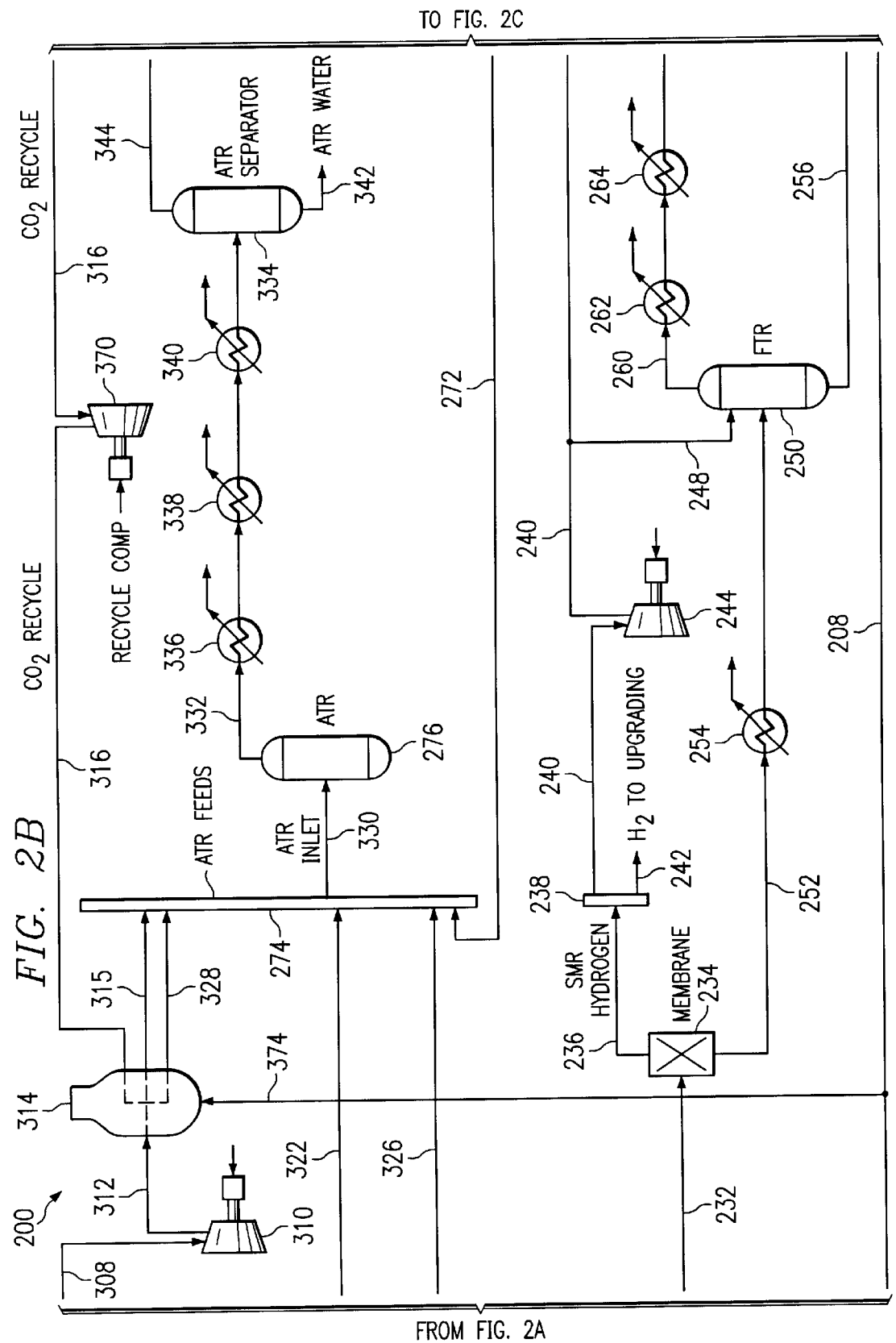
FIGS. 2 (A–C) is a schematic diagram of another embodiment of a system according to the present invention.

The preferred embodiment of the present invention and its advantages are best understood by referring to FIGS. 1 and 2 (A–C) of the drawings, like numerals being used for like and corresponding parts of the various drawings.

Referring to FIG. 1, a system 100 for converting light hydrocarbons into heavier hydrocarbons is shown having a first synthesis gas subsystem 12 that is fluidly coupled to a first synthesis system 14. As used herein, "fluidly coupled" means that two items are coupled in a way that fluid is allowed to communicate between the two, at least at the desired times. System 100 also has a second synthesis gas subsystem 16 that is fluidly coupled to a second synthesis subsystem 18.

In a preferred embodiment, the first synthesis gas subsystem or unit 12 is a steam methane reformer (SMR) system. Steam is delivered through inlet 20, and natural gas is delivered through inlet 22. It is to be understood that the feed streams (e.g., natural gas feed and steam) are conditioned, heated, and compressed as desired before being delivered. First synthesis gas subsystem 12 also receives a second tail gas through conduits 21 and 23. The origin of the second tail gas will be described below. The steam methane reformer 12 produces a first synthesis gas that has a high hydrogen-to-carbon-monoxide ratio, preferably about 2.5:1 to 4:1 and more preferably 3:1. For the higher range, a shift converter may be used to shift some of the CO to $CO_2$. The non-nitrogen diluted, first synthesis gas has a high hydrogen partial pressure and a high CO partial pressure.

This first synthesis gas is delivered through conduit 24 to a hydrogen separator unit 26, which may be, for example, a hydrogen membrane unit. The removed hydrogen is delivered to conduit 28 and optionally conduit 30. Conduit 28 delivers the hydrogen to the second synthesis subsystem 18 as will be described further below. In addition, a portion of the hydrogen may be removed through conduit 32 (shown in broken lines) to be delivered to first synthesis system 14 to adjust the hydrogen-to-carbon-monoxide ratio there if desired. The hydrogen optionally delivered to conduit 30 may be used elsewhere within system 100 or may be used for downstream processing. The first synthesis gas delivered from hydrogen separator 26 into outlet 34 preferably has a hydrogen to carbon monoxide ratio of about 2:1.

The first synthesis gas delivered through conduit 34 is used by the first synthesis subsystem 14 to produce Fischer-Tropsch products and preferably light (C18<) and heavy liquids (C18+), which are delivered for downstream processing or storage as represented by outlet conduit 36 going to storage 38. The first synthesis subsystem 14 also produces a first residual or tail gas that is delivered through conduit 40 to the second synthesis gas subsystem 16. The first tail gas is a non-nitrogen diluted gas, and because it has a relatively low carbon efficiency through the steam methane reformer, it has a significant amount of unreacted, unconverted methane in it. It also will have CO, $H_2$ and a little $CO_2$. The first tail gas thus makes a good feed stream for use in the second synthesis gas subsystem 16 as described further below.

Second synthesis gas subsystem 16 preferably includes an autothermal reformer. The second synthesis gas subsystem 16 receives an oxygen-containing gas (e.g., air or enriched air or $O_2$) through conduit 42. It also receives light hydrocarbons, which are preferably in the form of natural gas, through conduit 44. Steam 41 is also delivered to unit 16. The synthesis gas subsystem 16 also receives carbon dioxide ($CO_2$) through conduit 46. A second tail gas, whose origin will be described further below, is delivered through conduit 21 to second synthesis gas subsystem 16 and may be used as fuel for a burner, for example, to heat the oxygen-containing gas and/or natural gas. As discussed in connection with first synthesis gas subsystem 12, the feed streams are prepared or conditioned as desired before used. With these feed stocks, it produces a second synthesis gas that is delivered to conduit 48. As previously noted, the first tail gas in conduit 40 is also delivered to the subsystem 16 to be used as a feedstream for conversion.

Second synthesis subsystem 18 is fluidly coupled to second synthesis gas subsystem 16 by conduit 48 and receives the second synthesis gas therefrom. Second synthesis subsystem 18 converts the synthesis gas into heavier hydrocarbons preferably through a Fischer-Tropsch reaction. The heavy and light Fischer-Tropsch products may then go to storage and/or downstream processing. This is representatively shown by the products being delivered through conduit 50 to storage 38. Second synthesis subsystem 18 also produces a second tail gas that is delivered by conduit 52 to a $CO_2$ removal unit 54. $CO_2$ removal unit 54 removes all or a portion of the $CO_2$ and delivers the $CO_2$ to conduit 46. The $CO_2$ of conduit 46 is delivered to the second synthesis gas subsystem 16. Any remaining portion of the second tail gas is delivered to conduit 21 for uses previously mentioned.

The $CO_2$ delivered through conduit 46 allows the second synthesis subsystem 16, which preferably uses an autothermal reformer or POX, to have a higher carbon content than it otherwise would. Without further adjustment, the synthesis gas subsystem 16 would have less than the desirable 2:1 hydrogen-to-carbon-monoxide ratio to be used in the Fischer-Tropsch reactions (assuming a Co catalyst is used; the ratio would vary for other Fischer-Tropsch catalysts) of the second synthesis subsystem 18. A high-alpha cobalt catalyst is preferred for the synthesis subsystem. But, the steam methane reformer of the first synthesis gas subsystem 12 has a high hydrogen-to-carbon-monoxide ratio, and thus, a portion of the hydrogen may be removed and delivered to be included with the synthesis gas developed by second synthesis gas subsystem 16. The additional hydrogen, which is delivered by conduit 28, is preferably used to adjust the $H_2$:CO ratio to about 2:1. Further, the steam methane reformer of subsystem 12 combined with the first synthesis subsystem 14 does not generally provide relatively good single-pass conversion, but by delivering the unconverted tail gas through conduit 40 to the second synthesis gas subsystem 16, additional gains are realized.

Referring now to FIGS. 2 (2A–2C), a system 200 for converting light hydrocarbons to heavier hydrocarbons is presented. A steam methane reformer reactor (SMR) 202 receives light hydrocarbons, which are preferably in the form of natural gas, through conduit 204 and steam through conduit 206. The steam, and natural gas may be conditioned, heated, and compressed as desired before delivery. Any steam methane reformer design known in the art might be used. The steam methane reformer reaction typically includes a reformer catalyst within tubes that are indirectly fired and has reactions occurring in the tubes that are endothermic. Conduit 205 provides the combustion air for the heat source. The indirect heat is provided by radiant heat from a fire box or burner. Fuel to sustain the reaction within the steam reformer 202 is preferably provided at least in part by a second tail gas that is delivered through conduit 208. The synthesis gas developed in steam methane reformer 202 is delivered to conduit 210. The flue gas is discharged into conduit 211, which may include heat recovery elements 213. A plurality of coolers, such as coolers 212, 214, and 216, may be used to cool this first synthesis gas.

Conduit 210 delivers the first synthesis gas to a separator 218. The removed water in separator 218 may be delivered through conduit 220 to a water disposal unit (not shown) or stripped of dissolved gases and reused in the process. The effluent of separator 218 is delivered through conduit 222 to another separator 224 after additional cooling, such as by cross exchanger 226 and cooler 228. The water knocked out in separator 224 is delivered through conduit 230 to a water disposal unit (not shown) or stripped and reused.

The effluent of separator 224 is delivered through conduit 232 to a hydrogen removal unit 234. The hydrogen removal unit may be a membrane system, pressure swing absorption system or a combination system. The removed hydrogen is delivered through conduit 236 to junction 238 that delivers the hydrogen to conduits 240 and 242. The hydrogen delivered to conduit 242 may be delivered downstream of system 200 for upgrading of the resultant Fischer-Tropsch products. The hydrogen delivered to conduit 240 has its pressure stepped up by a booster compressor 244 and then is delivered to a mixer or junction 246 where it is mixed with a second synthesis gas as will be described further below. A portion of the hydrogen in conduit 240 may be removed through conduit 248 for use in a first Fischer-Tropsch reactor 250 to adjust the $H_2$:CO ratio.

The remaining portion of the first synthesis gas exits membrane 234, which is a hydrogen-reduced synthesis gas, through conduit 252 and is delivered to the first Fischer-Tropsch reactor 250. One or more heat exchangers such as heat exchanger 254 may be included on conduit 252. The heavy Fischer-Tropsch products developed by Fischer-Tropsch reactor 250 are delivered through conduit 256 to storage or for downstream processing as suggested by 258.

The light Fischer-Tropsch product effluent exits the Fischer-Tropsch reactor 250 through conduit 260, which includes a number of coolers such as 262 and 264. The cooled effluent is then delivered to separator 266. The water removed in separator 266 is delivered to conduit 268 for disposal or reuse. Liquid product is delivered through conduit 270 to storage or downstream processing as suggested by reference numeral 258. The residual gas, which is referred to as the first tail gas, is delivered through conduit 272 to a mixer manifold 274 where it is used as a fuel for an autothermal reformer(ATR) 276 as will be described further below. A booster compressor may be included in conduit 272 to step up the pressure of the first tail gas; for example, booster compressor 278.

Focusing on the ATR 276 (FIGS. 2A and 2B), an oxygen-containing gas (e.g., air or enriched air) is delivered to conduit 280. The air is prepared for use. The air is compressed by compressor 282 and delivered by conduit 284 to a separator/knockout 286 after being cooled by one or more coolers, such as coolers 288 and 290. The removed water is delivered to conduit 292, which delivers it to a water disposal unit or for stripping and reuse. The effluent of separator 286 is delivered through conduit 294 to another compressor (or compressor stage) 296. The compressed air exiting compressor 296 is delivered through conduit 298 to a second separator 300 after passing through one or more coolers, such as coolers 302 and 304. The water separated in separator 300 is delivered to conduit 306 that may deliver it to a water disposal unit or to be stripped and reused. The effluent of separator 300 is delivered through conduit 308 to compressor (or third compression stage) 310 to further compress the air. The air is then delivered through conduit 312 to heater unit 314 where it is heated and then the air is delivered through conduit 315 to the mixing manifold 274.

Light hydrocarbons, preferably in the form of natural gas, are delivered through conduit 318 to a natural gas preparation unit 320. Preparation unit 320 may include a number of filters and devices for removing catalyst poisons (e.g., sulfur) and for conditioning the natural gas. The prepared natural gas is delivered through conduit 322 to the mixing manifold 274. One or more heaters, such as heater 324, may be included on the conduit 322. Steam, which may be superheated or saturated, is delivered to conduit 326, which delivers it to mixing manifold 274

Manifold 274 thus combines the air (or other $O_2$-containing gas) delivered through conduit 315, carbon dioxide delivered through conduit 328 (the origin of which will be described further below), natural gas delivered through conduit 322, and steam delivered through conduit 326. The resultant feed stream is delivered through conduit 330 to ATR 276. The ATR 276 could also be a partial oxidation (POX) unit.

The ATR 276 produces a second synthesis gas that is delivered to conduit 332. Conduit 332 delivers the synthesis gas to a separator 334 after traveling through one or more coolers, such as coolers or heat recovery exchangers 336, 338 and 340. The water separated at separator 334 is delivered to conduit 342 from where it may go for reuse or to water disposal. The effluent of separator 334 is delivered by conduit 344 to mixer 246. From mixer 246, the first synthesis gas and the supplemental hydrogen delivered through conduit 240 are delivered through conduit 346 to second Fischer-Tropsch reactor 350. Heater 347 on conduit 346 may be used to heat the feed to within a desired range, which is preferably about 400 F. for this embodiment. Reactor 350 is shown as a single reactor, but it is to be understood that a number of reactors in series or parallel might be used. If more than one reactor is used in series, the hydrogen requirements for each reactor will increase as the synthesis gas goes further downstream.

The reactor 350 preferably uses a cobalt based catalyst (but other catalyst could be used). The second synthesis gas delivered through conduit 346 preferably has an adjusted hydrogen-to-carbon-monoxide ratio of approximately 2:1. The heavy Fischer-Tropsch products developed in Fischer-Tropsch reactor 350 are delivered through conduit 352 to storage or for downstream processing as represented by reference numeral 258.

The gaseous effluent of reactor 350 is delivered through conduit 354 to separator 356 after passing through one or more coolers, such as coolers 358 and 360. Water removed in separator 356 is delivered to conduit 362 from where it may go for reuse or to disposal. The liquid products separated in separator 356 are delivered to conduit 364 from where they are delivered to storage or for downstream processing as represented by reference numeral 258. The gaseous effluent of separator 356, which is a residual or tail gas, is delivered to conduit 366.

Conduit 366 delivers the residual gas or second tail gas to a carbon dioxide removal unit or scrubber 368. Carbon dioxide removal unit 368 may be any unit known in the art, but is preferably an amine-based absorption unit. The removed carbon dioxide is delivered to conduit 316. Conduit 316 delivers the carbon dioxide to heater 314 and then to manifold 274 from where it is introduced to the ATR. Conduit 316 may include a booster compressor 370. While not shown, in lieu of compressor 370, the carbon dioxide may be delivered further upstream to be compressed with air, such as being delivered to air inlet 280. The remaining portion of the second tail gas is delivered to conduit 208, which is fluidly coupled to steam methane reformer 202 where it may be used as fuel. A portion of the second tail gas may be removed from conduit 208 by conduit 374, which delivers a portion of the second tail gas to burner unit 314 for use as a burner fuel therein.

One of many possible examples of the operation of system 200 is now presented. In this regard, the temperatures and pressures mentioned are merely representative. The ATR of this embodiment is operated at a high pressure since the $CO_2$ recycle does not require a debit for the carbon efficiency loss at high pressure (normally one looses about 1% carbon efficiency for every 100 pounds of pressure increase). This way also eliminates the need for a synthesis gas compressor to step up the synthesis gas pressure before delivery to the Fischer-Tropsch reactor.

In operation, steam (at about 600 F. to 1000 F. and 500 psia) and natural gas (about 750 F. and 500 psia) are delivered to steam methane reformer 202 where a first synthesis gas is made. The first synthesis gas when made has a hydrogen-to-carbon-monoxide ratio of about 3:1. After cooling and separating, this gas is delivered to hydrogen removal unit 234. The removed hydrogen (about 120 F. and 400 psia) is delivered to Fisher-Tropsch reactor 350 to adjust the hydrogen-to-carbon-monoxide ratio of a second synthesis gas prepared in the autothermal reformer 276 to about 2:1. A portion to the hydrogen may also be used in Fischer-Tropsch reactor 250 or for downstream processing.

Once the hydrogen is removed from the first synthesis gas, the first synthesis gas has a hydrogen-to-carbon-monoxide ratio of about 2:1. This first synthesis gas (about 400 F and 432 psia) is delivered to Fisher-Tropsch reactor 250. The resultant heavier Fischer-Tropsch products are delivered to storage or for further processing 258. The first tail gas (about 100 F. and 359 psia) is delivered to ATR 276 after having been boosted in pressure as necessary.

Turning to the train with the ATR, after cleaning, heating, and compressing as necessary, air (about 1000 F. and 450 psia), natural gas (about 750 F. and 450 psia), steam, carbon dioxide (about 504 F and 450 psia), and the first tail gas (about 300 F. and 450 psia if compressed) are delivered to the ATR 276 where a second synthesis gas is prepared. Because of the carbon dioxide recycle, the hydrogen-to-carbon-monoxide ratio is lower than the preferred 2:1, but the second synthesis gas is mixed with hydrogen separated from the first synthesis gas as previously mentioned to adjust the ratio to the desired level. The second synthesis gas (at about 400 F. and 400 psia) is then delivered to the Fischer-Tropsch reactor 350. The resultant heavy Fischer-Tropsch product (C18+) is delivered to storage and/or downstream processing 258. The remaining tail gas after cooling and separation of light Fischer-Tropsch liquids is delivered to a carbon dioxide removal unit 368. The removed carbon dioxide is delivered to ATR 276 as previously noted. The carbon dioxide may be boosted in pressure as necessary. The remaining portion of the gaseous product delivered to carbon dioxide removal unit 368 forms the second tail gas that may be used as a burner fuel in the SMR 202 and/or a heater 314 associated with the ATR 276.

It will be appreciated that the carbon dioxide recycle provides improved carbon efficiency. With the carbon dioxide recycle, the ATR approaches 100 percent carbon efficiency, and thus the overall carbon efficiency of the second synthesis gas source and second Fischer-Tropsch reactor subsystem is about 80–85 percent. The recycled carbon dioxide produces carbon monoxide through a reverse water gas shift. This represents as much as a 20 percent decrease in the amount of natural gas required to produce a given quantity of product. The problem of the carbon dioxide recycle lowering the hydrogen-to-carbon-monoxide ratio is remedied by the use of excess hydrogen in the synthesis gas prepared in the steam methane reformer.

The systems and methods of the present invention are preferably used to convert synthesis gas into longer-chain hydrocarbons, e.g., the full spectrum of $C_{5+}$ products through the Fischer-Tropsch reaction (but the invention further may have application with non-Fischer-Tropsch processes). The Fischer-Tropsch products that may be made directly or with downstream processing include numerous products for numerous uses.

Although the present invention and its advantages have been described in detail, it should be understood that various changes, substitutions and alterations can be made therein without departing from the spirit and scope of invention as defined by the appended claims. For example, system 200 is shown with two different synthesis gas sources 202 and 276, but it is to be understood that additional and/or other synthesis gas sources might be used as well. Also, portions of one embodiment may be adapted and used with other suggested embodiments. As another example, while only one Fischer-Tropsch reactor is shown for each train, a plurality of reactors may be used.

What is claimed is:

1. A Fischer-Tropsch-based process for converting light hydrocarbons into heavier hydrocarbons ($C_{5+}$), the process comprising the steps of:

preparing a first synthesis gas having an $H_2$:CO ratio greater than 2:1;

removing a portion of the hydrogen from the first synthesis gas;

preparing a second synthesis gas, wherein the step includes using a $CO_2$ recycle stream and wherein the second synthesis gas has a $H_2$:CO ratio less than 2:1;

adding the removed hydrogen to the second synthesis gas to increase the $H_2$:CO ratio of the second synthesis gas; and using a Fischer-Tropsch reaction to convert the first synthesis gas and the second synthesis gas into heavier hydrocarbons.

2. The process of claim 1 wherein the step of preparing a first synthesis gas comprises the step of preparing a first synthesis gas using a steam methane reformer.

3. The process of claim 1 wherein the step of preparing a second synthesis gas comprises the step of preparing a second synthesis gas using an autothermal reformer.

4. The process of claim 1 wherein the step of preparing a first synthesis gas comprises the step of preparing a first synthesis gas using a steam methane reformer and wherein the step of preparing a second synthesis gas comprises the step of preparing a second synthesis gas using an autothermal reformer.

5. The process of claim 1 wherein the step of removing a portion of the hydrogen from the first synthesis gas includes the step of removing enough hydrogen from the first synthesis gas to arrive at an $H_2$:CO ratio of about 2:1 in the first synthesis gas; wherein the step of adding the removed hydrogen to the second synthesis gas includes the step of adding enough hydrogen to the second synthesis gas to arrive at an $H_2$:CO ratio of about 2:1; and wherein the step of using a Fischer-Tropsch reaction includes the step of using a cobalt Fischer-Tropsch catalyst.

6. A process for converting light hydrocarbons into heavier hydrocarbons ($C_{5+}$), the process comprising the steps of:

using a first synthesis gas unit to prepare a first synthesis gas having a $H_2$:CO ratio greater than 2:1;

using a second synthesis gas unit, which has a $CO_2$ recycle, to prepare a second synthesis gas, wherein the second synthesis gas has a $H_2$:CO ratio less than 2:1;

removing a portion of the hydrogen from the first synthesis gas;

adding the removed hydrogen to the second synthesis gas to increase the $H_2$:CO ratio of the second synthesis gas;

using a first Fischer-Tropsch synthesis unit to convert the first synthesis gas into heavier hydrocarbons and a first tail gas;

using a second Fischer-Tropsch synthesis unit to convert the second synthesis gas into heavier hydrocarbons and a second tail gas;

removing $CO_2$ from the second tail gas;

delivering the removed $CO_2$ to the second synthesis gas unit for use therein in producing the second synthesis gas.

7. The process of claim 6 further comprising the step of delivering a portion of the removed hydrogen to the first synthesis unit for $H_2$:CO ratio control therein.

8. The process of claim 6 further comprising the step of delivering at least a portion of the first tail gas for use in preparing the second synthesis gas.

9. The process of claim 6 further comprising the steps of using the second tail gas as a burner fuel in the first synthesis gas unit.

10. The process of claim 6 further comprising the steps of:

using the removed hydrogen in the first synthesis unit for $H_2$:CO ratio control therein;

using at least a portion of the first tail gas as a feed stock in the second synthesis gas unit; and using the second tail gas after $CO_2$ removal in the first synthesis gas unit as a burner fuel therein.

11. The process of claim 6 wherein the step of removing a portion of the hydrogen from the first synthesis gas includes the step of removing enough hydrogen to adjust the $H_2$:CO ratio of the first synthesis gas to about 2:1; wherein the step of adding the removed hydrogen to the second synthesis gas includes the step of adding a sufficient quantity of hydrogen to adjust the $H_2$:CO ratio of the second synthesis gas to about 2:1; and wherein the steps of using a first Fischer-Tropsch synthesis unit and using a second Fischer-Tropsch synthesis unit both include the step of using a cobalt Fischer-Tropsch catalyst.

* * * * *